US005749841A

United States Patent [19]
Moore

[11] Patent Number: 5,749,841
[45] Date of Patent: May 12, 1998

[54] WRIST BRACE WATCH

[76] Inventor: Jay Gary Moore, 720 W. Shubert Ave., Chicago, Ill. 60614

[21] Appl. No.: 478,871

[22] Filed: Jun. 7, 1995

[51] Int. Cl.⁶ .................................. A61F 5/00
[52] U.S. Cl. .................. 602/21; 602/20; 602/64
[58] Field of Search ................... 602/5, 21, 64, 602/20; 368/10, 281–283, 286; 224/164, 167, 168, 177, 180; 2/20, 160, 161.1

[56] References Cited

U.S. PATENT DOCUMENTS

| | | | |
|---|---|---|---|
| D. 249,939 | 10/1978 | Dammons | D11/2 |
| D. 330,679 | 11/1992 | Bland | D10/32 |
| 1,271,735 | 7/1918 | Lockwood | . |
| 2,249,550 | 7/1941 | Williams | 58/105 |
| 2,482,660 | 9/1949 | Dewey | 368/282 X |
| 4,086,916 | 5/1978 | Freeman et al. | 128/661.07 |
| 4,149,662 | 4/1979 | Ranaciere | 224/164 |
| 4,213,548 | 7/1980 | Wood | 224/168 |
| 4,387,838 | 6/1983 | Jackson | 224/170 |
| 4,652,141 | 3/1987 | Arai | 368/278 |
| 4,681,462 | 7/1987 | Lloyd | 224/164 X |
| 4,685,599 | 8/1987 | Israel et al. | 224/170 |
| 4,766,611 | 8/1988 | Kim | 2/160 |
| 4,769,799 | 9/1988 | Matsukage | 368/278 |
| 5,003,637 | 4/1991 | Lonon | 2/160 |
| 5,068,840 | 11/1991 | Buckner | 368/281 |
| 5,117,508 | 6/1992 | Gurte | 2/160 |
| 5,160,314 | 11/1992 | Peters | 602/64 X |
| 5,205,449 | 4/1993 | Davies | 224/152 |
| 5,267,943 | 12/1993 | Darcyger | 602/21 X |
| 5,313,667 | 5/1994 | Levine | 2/160 |
| 5,376,066 | 12/1994 | Phillips et al. | 602/64 |

FOREIGN PATENT DOCUMENTS 9119426  12/1991  WIPO ........................... 2/160

*Primary Examiner*—Lynne A. Reichard
*Assistant Examiner*—Denise Pothier
*Attorney, Agent, or Firm*—Leydig, Voit & MayerLTD

[57] ABSTRACT

Time piece incorporated into a wrist brace to allow one to wear the wrist brace and a time piece. The invention comprises a wrist brace having a support web typically secured on the wrist by a strap which has a VELCRO® strip which is secured to a VELCRO® strip on the web. The time piece assembly comprises a looped band which has a two VELCRO® strips, one for engaging the VELCRO® strip on the web, the other for engaging the VELCRO® strip on the strap. The time-piece is operable from a control panel within the reach of the fingers on the hand extending from the wrist on which the wrist brace is worn.

6 Claims, 3 Drawing Sheets

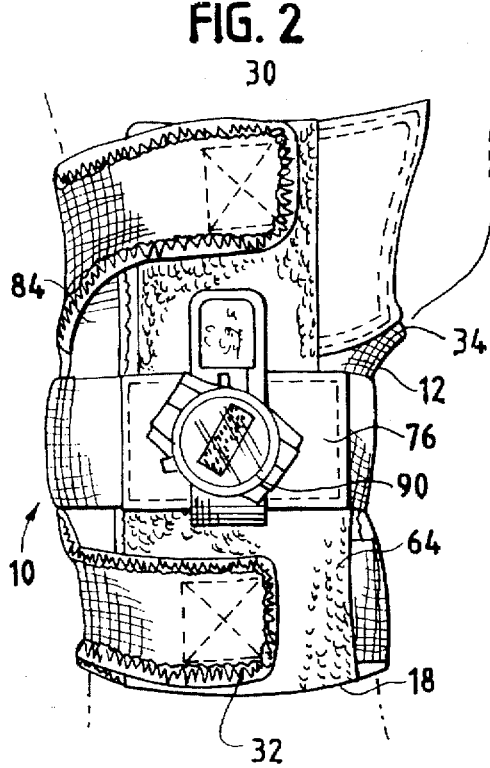
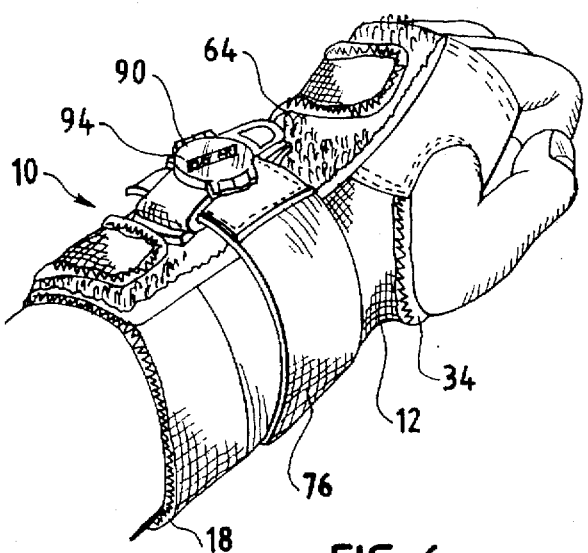
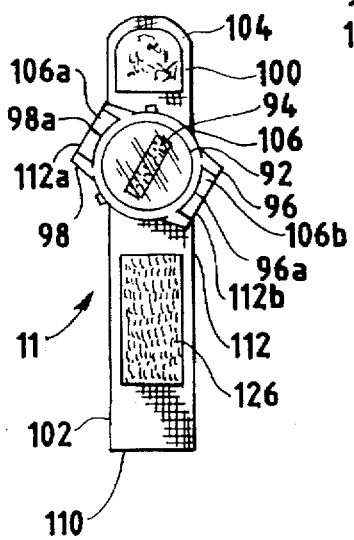
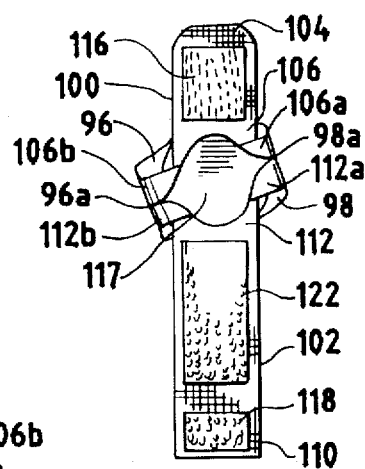
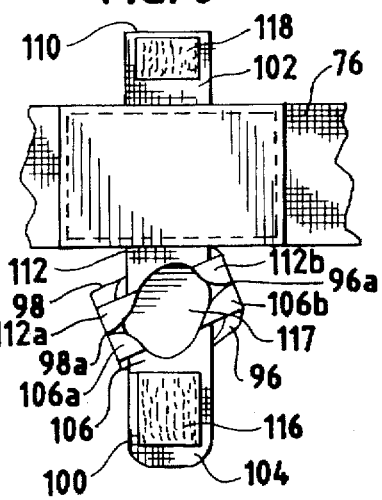
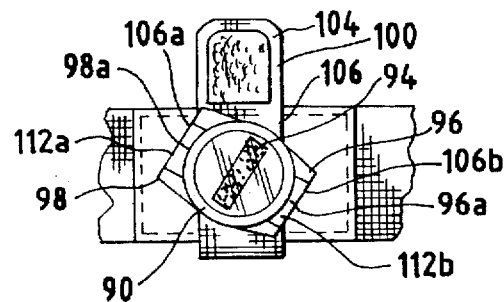

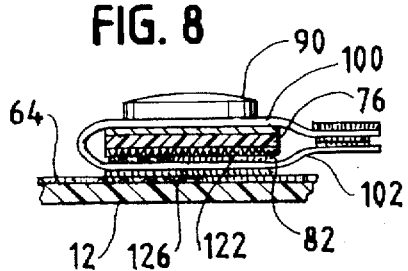
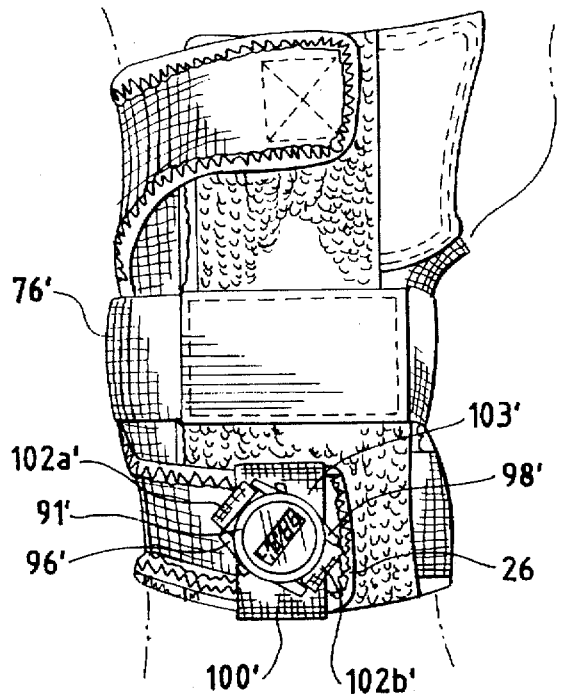
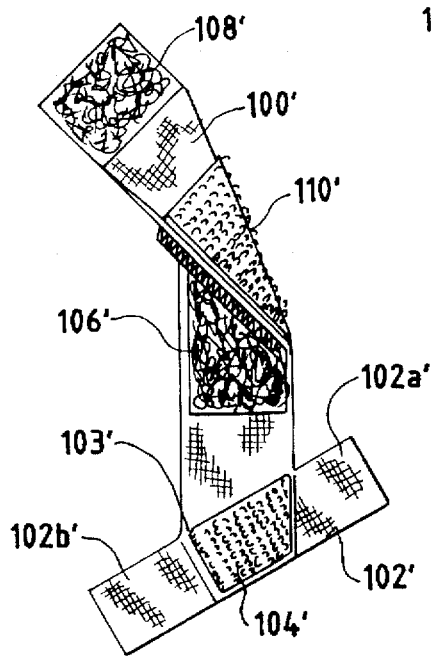
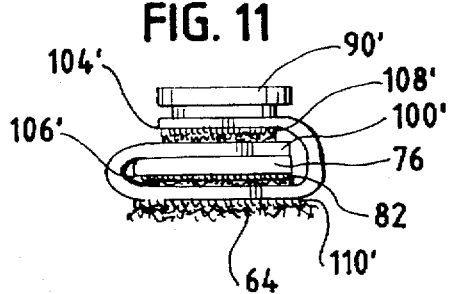
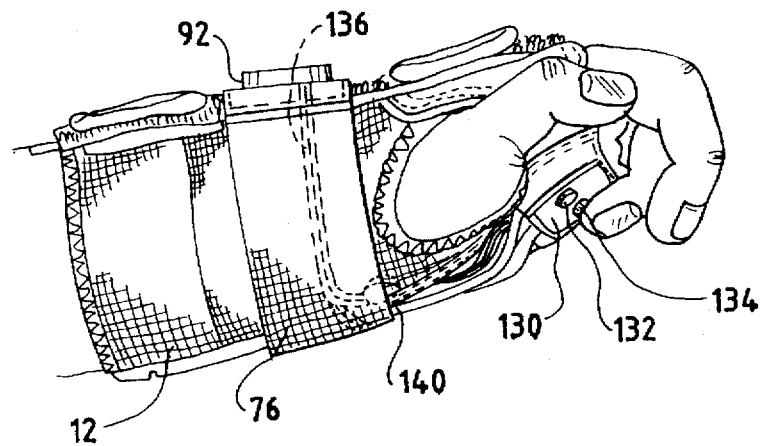

WRIST BRACE WATCH

INTRODUCTION

1. Field Of The Invention

This invention relates to a device for isolating, stabilizing or insulating a person's wrist against injury and concurrently accommodating a time piece.

2. Discussion of the Prior Art

People wear wrist braces for several reasons. People often wear wrist braces to isolate, insulate or stabilize the wrist after the wrist has been injured. People also frequently wear wrist braces to prevent wrist injury by stabilizing the wrist against extreme bending, usually caused by some type of unanticipated impact. With the increasing popularity of in-line skating, more people are wearing wrist braces for this latter purpose of preventing wrist injury.

Recreational in-line skating often involves skaters approaching relatively high speeds along sidewalks or streets on which obstacles in the pavement, other skaters, pedestrians and motorized vehicles can cause the skater to lose his balance and fall. Upon loss of balance, skaters naturally interpose their hands between themselves and the ground or other surface to try to cushion or stop their fall, thereby exposing their wrist to impact and risking injury. Many skaters appreciate this risk and prudently wear wrist braces to secure their wrists against abrupt bending which can sprain, brake or otherwise injury the wrist.

When one wears a wrist brace on an arm, it is difficult to wear a wrist watch on the same arm. To wear the wrist watch under the wrist brace is uncomfortable, not to mention the fact that the face of the watch would not be easily discernible under the wrist brace. Wrist watches do not normally have bands large enough to fit entirely around the wrist brace when it is worn on the wrist. Similarly, the bands of normal wrist watches do not easily fit around the upper arm and if it does, such an arrangement can uncomfortably constrict the muscles of the upper arm, which are normally flexing while the skater is moving his arms for balance or to propel himself for speed. Moreover, strapping the watch around the upper arm requires the wearer to move his head to look high on the arm to observe the time piece thereby diverting his attention from the road way and raising the possibility of losing his balance.

Accordingly, if one wears a wrist brace on the arm, he encounters several problems with wearing a wrist watch on the same arm. If one insists on wearing a wrist watch, he often forfeits wearing a wrist brace on that arm and takes the risk of leaving the particular wrist unprotected. The present invention solves these problems.

An object of this invention is to provide a wrist brace which will protect the wrist against injury and accommodate a time piece.

Another object of this invention is to obviate the difficulties and problems one encounters while wearing a wrist watch and a wrist brace at the same time.

A further object of the invention is to provide a time piece assembly that can be incorporated into the typical wrist brace.

A still further object of the invention is to provide a means for operating the time piece incorporated into the wrist brace with the hand on the wrist on which the brace is worn.

SUMMARY OF THE INVENTION

The present invention incorporates a time piece into a wrist brace to allow one to wear the wrist brace and a time piece, thus protecting the wrist and allowing the wearer to keep track of time, without encountering the foregoing problems. The invention comprises a wrist brace having a support web typically secured on the wrist by straps having VELCRO® strips which mate with VELCRO® strips on the web. When the wrist brace is applied around the wrist, it has the general configuration of a tube. The time piece assembly comprises a looped band which has VELCRO® strips which mate with the VELCRO® strips on the wrist brace and the VELCRO® strips on the straps to secure the time piece assembly to the wrist brace. A means for operating the time piece with the hand wearing the wrist brace is also provided in the present invention.

BRIEF DESCRIPTION OF THE DRAWINGS

The foregoing and other novel features and advantages of the invention will be better understood upon a reading of the following Detailed Description taken in conjunction with the accompanying drawings wherein:

FIG. 2 is a top perspective view of the wrist brace with time piece assembly in FIG. 1 in a closed condition around a wrist;

FIG. 3 is an angled perspective view of the wrist brace with time piece assembly in FIG. 2;

FIG. 4 is a top plan view of a time piece assembly of FIG. 3;

FIG. 5 is a bottom plan view of the time piece assembly of FIG. 4;

FIG. 6 is a bottom plan view of the time piece assembly of FIG. 5 engaged to a strap from the wrist brace of FIG. 1;

FIG. 7 is a bottom plan view of the time piece assembly of FIG. 6 in a folded condition;

FIG. 8 is a cross-section view of the time piece assembly in FIG. 7;

FIG. 9 is a top perspective view of an alternative embodiment of the wrist brace with time piece assembly in FIG. 2;

FIG. 10 is a perspective view of two bands used in the alternative embodiment in FIG. 9;

FIG. 11 is a cross section view of the time piece assembly in FIG. 9; and

FIG. 12 is a side perspective view of the wrist brace with time piece assembly in FIG. 2.

DETAILED DESCRIPTION

Figure 1:
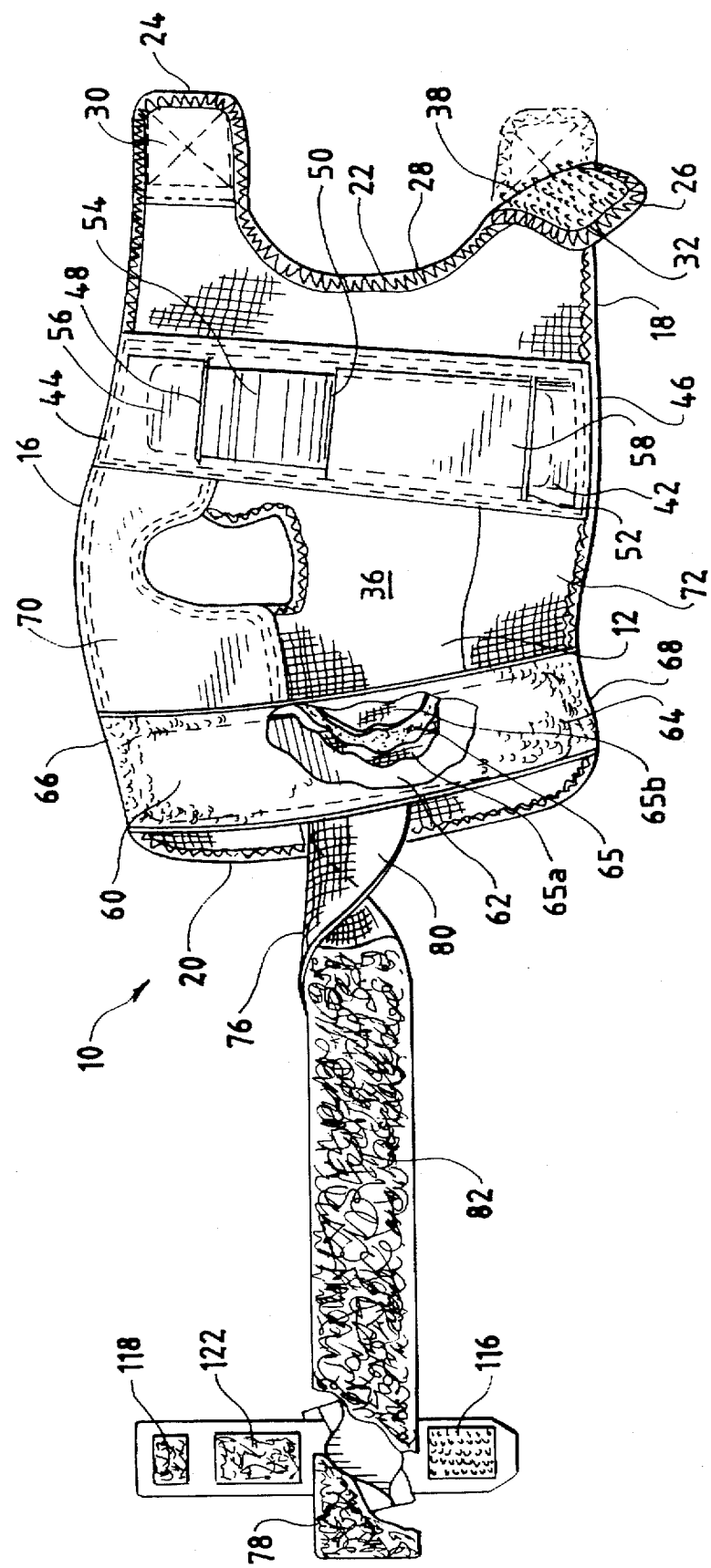
FIG. 1 is a perspective view of the wrist brace with time piece assembly of the present invention in an open condition with two break away portions to show detail.

The present invention comprises a time piece incorporated into a wrist brace. The wrist brace can be of any standard type, including braces for stabilizing or insulating an injured wrist and braces for protecting the wrist against injury which could result from a forceful impact. By way of illustration the invention will be described in conjunction with a wrist brace used by skaters to protect their wrists in the event that the skater falls on one or both of his wrists which frequently results in an injury to the impacted wrist.

A wrist brace 10 for skaters utilized in the present invention is shown in FIG. 1 in an open condition. The wrist brace 10 comprises a web 12 made of porous, flexible material. The web 12 has four primary edges including a top edge 16, a bottom edge 18 and a left edge 20 which are all basically straight and a right edge 22 which is not straight. The right edge 22 has a top straight edge portion 24 adjacent to the top edge 16, a bottom straight edge portion 26 adjacent to the bottom edge 18 and a semicircular cutout edge 28 between the top straight edge potion 24 and the bottom straight edge portion 26. The material between the top edge 16, the top straight edge portion 24 and the semicircular cutout edge 28 comprises a top tie 30. The material between the bottom edge 18, the bottom straight edge portion 26 and the semicircular cutout edge 28 comprises a bottom tie 32. The web 12 includes a rounded cutout near the top edge 16 defined by a rounded edge 34. All of the foregoing edges are supported with a stitched border seam to strengthen the edges.

The web 12 has an inner surface (not shown) and an outer surface 36. A strip of VELCRO® hooks (not shown) is connected to the inner surface of the top tie 30, and a strip 38 of VELCRO® hooks is connected to the inner surface of the bottom tie 32 by a series of stitches.

A first envelope 42 comprising two plies of leathery material such as vinyl is adjacent to the semicircular cutout edge 28 of the right edge 22. The first envelope 42 is connected to the outer surface 36 by a series of stitches along the outer edges of the first envelope 42. A top edge 44 of the first envelope 42 is adjacent to the top edge 16 of the web 12, and a bottom edge 46 of the first envelope 42 is adjacent to the bottom edge 18 of the web 12. Three slits are formed in a top ply of the leathery material, a top slit 48 one near the top edge 16, a center slit 50 near the center of the first envelope 42 and a bottom slit 52 near the bottom edge 18.

A first angled reinforcement prop 54 with a width that is less than the width of the first envelope 42 has a top arm 56 that slides into the top slit 48 between the two plies of leathery material comprising the first envelope 42. A bottom arm 58 of the reinforcement prop 54 slides into the center slit 50 between the two plies of leathery material. A first resilient foam pad (not shown) is inserted between the bottom ply of leathery material of the first envelope 42 and the web 12.

Adjacent the left edge 20 of the web 12 is a second envelope 60 similar to the first envelope 42 which houses a second reinforcement prop 62 shown by the cut away portion in FIG. 1. The second reinforcement prop 62 is angled but not to the same extent as the first reinforcement prop 54. The second envelope 60 sandwiches the second reinforcement prop 62 between a strip 64 of VELCRO® loops and a foam pad 65. The foam pad 65 is sealed between two laminates 65a, 65b of the material comprising the web 12.

The second envelope 60 is stitched to the outer surface 36 of the web 12 along the outer edges of the second envelope 60. A top edge 66 of the second envelope 60 is adjacent to the top edge 16 of the web 12 and a bottom edge 68 of the second envelope is adjacent to the bottom edge 18 of the web 12. The second reinforcement prop 62 is completely enclosed by the second envelope 60, unlike the first reinforcement prop 54 which is accessible through the slits 48, 50 and 52 in the first envelope 42.

A ribbon 70 of leathery material such as vinyl is stitched to a portion of the outer surface 36 of the web 12 constrained essentially by the first envelope 42, the top edge 16 of the web 12, the second envelope 60 and the rounded edge 34 to lend support to the wrist brace 10. A strip 72 of fortifying material such as nylon is stitched to the outer surface 36 of the web 12 adjacent the bottom edge 18 between the first envelope 42 and the second envelope 60.

The wrist brace 10 is secured with a long strap 76 of strong material such as nylon having a remote end 78 and a proximate end 80. The proximate end 80 is securely connected to the second envelope 60 and the web 12 by a series of stitches. A strip 82 of VELCRO® hooks is attached to a bottom side of the strap 76 extending from the remote end 78 to short of the proximal end 80. The strip 82 of VELCRO® hooks extends to short of the proximal end to avoid annoying contact between the strip 82 of VELCRO® hooks and the flesh of the wrist 84 not covered by the web 12 when the wrist brace 10 is worn as shown in FIG. 2.

To wear the wrist brace 10, one inserts his thumb into the cutout defined by the rounded edge 34, so the bottom edge 18 of the web 12 is facing him. The top tie 30 and the bottom tie 32 are tightly rolled to generally form a tube around the hand and forearm, respectively, as shown in FIGS. 2 and 3. The strips of VELCRO® hooks on the inner side of the top tie 30 and the bottom tie 32 engage the strip 64 of VELCRO® loops on the second envelope 60. The long strap 76 is wrapped around the wrist brace 10 in the opposite orientation as the top tie 30 and the bottom tie 32 and the strip 82 of VELCRO® hooks engages the strip 64 of VELCRO® loops on the second envelope 60.

The first reinforcement prop 54 and the second reinforcement prop 60 of the wrist brace 10 prevent the hand of the wearer from bending beyond a predetermined degree in a forward or backward direction, respectively, to thereby maintain the wrist 84 in an essentially stationary condition.

The present invention provides for incorporating a time piece 90 on the wrist brace 10. The time piece 90 can be located at a variety of locations on the wrist brace 10. For an ordinary wrist brace 10 it may be acceptable to locate the time piece 90 on top or on the bottom of the wrist brace 10, so the wearer could refer to the time piece 90 by doing no more than he would to refer to a wrist watch; i.e., elevating the forearm and rotating wrist so the time piece 90 is directed toward the eyes of the wearer.

As shown in FIG. 4, time piece assemblies 91 normally comprise a body 92, with a display 94 and two dowel assemblies 96, 98 affixed to the body. The dowel assemblies 96, 98 are located at the top and bottom of the body 92 with respect to the display 94. A first band 100 and a second band 102 are affixed to the dowel assemblies 96, 98, respectively.

I have determined that when one is wearing the wrist brace 10 while skating, and particularly while racing on skates, skaters move each of their arms individually to a position which simulates the position of the arm of a diver who is preparing to make a dive as shown in FIG. 3. To make it easy to observe the display 94 on time piece 90 while skating, it is preferred to rotate the time piece 90 counter-clockwise by 60° with respect to the bands 100, 102 as shown in FIGS. 3 and 4. Hence, the observation of the time piece 90 by the wearer does not require the wearer to break the stride of his natural arm movement while skating.

The following structure allows one to utilize conventional time pieces 90 with the dowel assemblies 96, 98 at the top and bottom of the body 92, to present the display 94 at the 60° rotation to provide ease of observation. With reference to FIGS. 4 and 5, the time piece assembly 91 includes a first band 100 with a solid end 104 and a split end 106 and a second band 102 with a solid end 110 and a split end 112. An arm 106a of the split end 106 of the first band 100 is threaded around a dowel 98a in the dowel setting 98, doubled back and bonded to the first band 100, and an arm 106b of the split end 106 of the first band 100 is threaded around a dowel 96a in the dowel setting 96, doubled back and bonded to the first band 100. The arm 106a is shorter than the arm 106b to provide the 60° orientation for the body and display. An arm 112a of the split end 112 of the second band 102 is threaded around the dowel 98a in the dowel setting 98, doubled back and bonded to the second band 102, and an arm 112b of the split end 112 of the second band 102 is threaded around the dowel 96a in the dowel setting 96, doubled back and bonded to the second band 102. The arm 112a is longer than the arm 112b to accommodate the lengths of arms 106a, 106b, respectively, and to provide the 60° orientation of the display 94.

Although the time piece 90 can be attached directly to the web 12, strap 76 or any other location on the wrist brace 10, I prefer to incorporate the time piece 90 into wrist brace 10 at the connection between the strip 82 of VELCRO® hooks on the remote end 78 of the strap 76 and the strip 64 of VELCRO® loops on the second envelope. This arrangement allows the time piece assembly 91 to be easily attached and easily removed from the wrist brace 10 if desired.

Alternatively, the time piece assembly 91 can be attached to a single band, instead of a first and second band 100, 102, by an adhesive or any other attaching means. If a single band is used, a circular cutout (not shown) in the band where the body 92 of the time piece 90 is attached to the band allows access to a back panel 117 of the time piece 90, whereby the panel 120 can be removed for admission to the contents inside the time piece 90.

A strip 116 of VELCRO® hooks is attached to an inner surface of the solid end 104 of the first band 100, and a strip 118 of VELCRO® loops is attached to the inner surface of the solid end 110 of the second band 102. A second strip 122 of VELCRO® loops is attached to the inner surface of the second band 102 adjacent to the strip 118 of VELCRO® loops. A strip 126 of VELCRO® hooks is attached to outer surface of the second band 102.

To install the time piece assembly 91 on the wrist brace 10, the second strip 122 of VELCRO® loops on the inner surface of the second band 102 is engaged to the strip 82 of VELCRO® hooks on the strap 76 as shown in FIG. 6. The first strip 116 of VELCRO® hooks on the inner surface of the first band 100 is folded to engage the first strip 118 of VELCRO® loops on the inner surface at the solid end 110 end of the second band 102 as shown in FIG. 7.

The wrist brace 10 is then put on the same way as if the time piece assembly 91 was not on the strap 76 as previously described, except for when the strap 76 is wrapped around the wrist brace 10. Instead of the strip 82 of VELCRO® hooks on the strap 76 engaging the strip 64 of VELCRO® loops on the second envelope 60, the strip 82 of VELCRO® hooks is already engaged with the second strip 122 of VELCRO® loops on the inner surface of the second band 102. Hence, the strip 126 of VELCRO® hooks on the outer surface of the second band 102 are engaged with the strip 64 of VELCRO® loops on the second envelope 60 as shown in FIGS. 2 and 3.

The present invention also contemplates other arrangements for putting the time piece assembly 91 on the wrist brace 10. The time piece assembly can be installed on either of the top tie 24 or the bottom tie 28, similar to the way the time piece 90 is attached to the strap. As shown in FIG. 9, a time piece assembly 91' is attached to the bottom tie 32. The structure of the band for this arrangement is shown in FIG. 10.

A first band 100' intersects a second band 102' at intersection 103' to form a slanted T-shape. Two arms 102a' and 102b' extend from band 102' to be threaded through the dowel settings 96' and 98', respectively, of the time piece assembly 91'. A strip 104' of VELCRO® hooks is attached to an inner surface of the band 100' at the intersection 103' of bands 100' and 102' and a strip 106' of VELCRO® loops is attached to band 100' on the inner surface adjacent strip 104'. A strip 108' of VELCRO® loops is attached to the outer surface of the band 100' at an end remote from the intersection 103' of the band 100' and the band 102'. A strip 110' of VELCRO® hooks is attached to the outer surface of the band adjacent strip 108'.

To install time piece assembly 91' to the wrist brace 10, the ends of two arms 102a' and 102b' of band 102' are threaded through the dowel settings 96' and 98', respectively, of the time piece assembly 91', doubled back and bonded to the respective arms 102a' and 102b'. The strip 106' of VELCRO® loops engages the strip 32 of VELCRO® hooks on the bottom tie 26, the band 100' is folded over the tie 26 first and then the intersection 103' of the bands 100' and 102' is folded over the tie 26, so that strip 104' of VELCRO® hooks engages the strip 108' of VELCRO® loops to secure the time piece assembly 91' on the tie 26. The strip 110' of VELCRO® hooks then engages the strip 64 of VELCRO® loops on the second envelope 60 as shown in FIGS. 10 and 11.

Although, it is preferred to locate the time piece 90 at the remote end 78 of the strap 76, which is situated above the wrist brace 10 while the brace 10 is worn, the strap 76 is constructed with a strip 82 of VELCRO® hooks which extends from the remote end 78 of the strap 76 to short of the proximate end 80 of the strap 76. With this construction, the time piece assembly 91 can be located at several locations on the circumference of the wrist brace 10.

The time piece assembly 91 is located on the strap 76 at a position away from the strip 64 of VELCRO® loops on the second envelope 60, by mating the second strip 122 of VELCRO® loops on the inner surface of the second band 102 of the time piece assembly 91 with the strip 82 of VELCRO© hooks on the strap 76. The strip 126 of VEL-CRO® hooks on the outer surface of the second band 102 will not engage the strip 64 of VELCRO® loops in this position, but instead the strip 82 of VELCRO® hooks on the strap 76 will engage the strip 64 of VELCRO® loops on the second envelope 60 on the web 12.

To enhance the functionality of the time piece 90, the present invention includes appending a control panel 130 to the outer surface of the web 12 at the top edge 16 adjacent the first envelope. The buttons 132, 134 on the control panel 130 face in the same direction as the outer surface of the web 12, to allow the wearer to operate the buttons 132, 134 by doubling back his fingers as shown in FIG. 12. The buttons 132, 134 on the control panel 130 are linked with circuitry such as wires 136 to a processing unit (not shown) within the body 92 of the time piece 90, so the wearer can manipulate the operation of the time piece 90 by manipulating the buttons 132, 134 with his fingers. The buttons 132, 134 may comprise any conventional means including heat sensitive surfaces, rheostats, etc.

Conventional time pieces may be used in the present invention. It is contemplated that the time piece 90 be an electrical device with a computerized processing unit, a display 94 and provide at least one or none of the following functions: time, date, stopwatch with start, stop, lap and reset features, alarm, calendar, pulse monitor, mode control for setting the foregoing features, etc. One of ordinary skill in the art of time pieces will be familiar with the design and operation of the time piece 90 incorporated into my invention.

As previously described, it is preferred to rotate the face of the display 60°. The display alternatively may be rotatable to adjust the display to any desire degree.

The present invention also contemplates that a pulse monitor function in the time piece 90 be interconnected to a sensor 140 which can be positioned at an appropriate position on the wearer's body, such as the wrist, to monitor the pulse of the heart. The sensor can also be positioned on other parts of the body to monitor other bodily functions or connected to an apparatus which monitors other bodily functions or other dynamic events and signals these functions or events to the processing unit in the time piece 90, which then interprets and registers these functions or events on the display.

Although the invention has been described in conjunction with the foregoing specific embodiments, many alternatives, variations, and modifications will be apparent to those of ordinary skill in the art. Those alternatives, variations, and modifications are intended to fall within the scope of the appended claims.

I claim:

1. A wrist brace comprising: a flexible tube having an inner surface and an outer surface, said inner surface of said tube having sufficient diameter to encompass a wrist of a person wearing said brace, a front open end in said tube through which the fingers of said person may extend and a rear open end in said tube through which the forearm of said person may extend, said tube comprising a web with a first edge and a second edge which, while in an open position said web can loosely cover said wrist, a part of said hand and a part of said forearm, and when said first edge and said second edge of said web are rolled near to each other into a closed position to form said tube, said tube can securely encompass said wrist, a part of said hand and a part of said forearm, a top side of said tube which is generally disposed above said wrist when said wrist brace is being worn by said person and a bottom side of said tube which is disposed generally below said wrist when said wrist brace is being worn by said person;

at least one elongated reinforcement member made of substantially rigid material for supporting said wrist against excessive bending and being housed along said tube outside said inner surface;

a strip of multiple tiny loops attached to said tube;

at least one strap having a proximal end attached adjacent to one of said first edge and said second edge, said strap having a strip of multiple tiny hooks thereon which can securely engage said multiple tiny loops on said tube to attach said strap to said outer surface of said tube to maintain said web in said closed position;

a looped band for receiving a remote end of said strap therethrough, a strip of multiple tiny loops being attached to an interior surface of said looped band for engaging said multiple tiny hooks on said strap to secure said loosed band to said strap, and a strip of multiple tiny hooks being attached to an exterior surface of said looped band for engaging said strip of multiple tiny loops on said tube to secure the looped band to said tube, thereby also securing the remote end of said strap to said tube, said looped band comprising a first band with a proximate end and a remote end and a second band with a proximate end and a remote end;

a time piece attached to an exterior surface of said looped band, said time piece including a first dowel setting supporting a first dowel and a second dowel setting supporting a second dowel each on opposed sides of said time piece, said proximate end of said first band being secured to said first dowel and said proximate end of said second band being secured to said second dowel, a strip of multiple tiny hooks attached to said remote end of said first band which engages a strip of multiple tiny loops on said remote end of said second band, and said proximate end of said first band being split into a first arm and a second arm and said first arm attaches to said first dowel and said second arm attaches to said second dowel.

2. The wrist brace of claim 1 wherein said first arm of said first band is shorter than said second arm of said first band, so that said time piece is set at an angle with respect to an imaginary axis through the longitudinal center of said first and and said second band.

3. The wrist brace of claim 1 wherein said looped band has a proximate end and a remote end, a first arm extends outwardly from said proximate end of said looped band and secures said first dowel and a second arm extends outwardly from said proximate end and secures said second dowel to attach said time piece to said proximate end; and a strip of multiple tiny hooks being attached to said proximate end of said band to engage a strip of multiple tiny loops attached to said remote end of said band to form a closed loop.

4. The wrist brace of claim 3 wherein said first arm and said second arm are angled with respect to said band, so the time piece is assembled at an angle with respect to said band.

5. A wrist brace comprising:

a flexible tube having an inner surface and an outer surface, said inner surface of said tube having sufficient diameter to encompass a wrist of a person wearing said brace; a front open end in said tube through which the fingers of said wrist may extend and a rear open end in said tube through which the forearm of said person may extend, said tube comprising a web with a first edge and a second edge which, while in an open position said web can loosely cover said wrist, a part of said hand and a part of said forearm, and when said first edge and said second edge of said web are rolled near to each other into a closed position to form said tube, said tube can securely encompass said wrist, a part of said hand and a part of said forearm, and a top side of said tube which is generally disposed above said wrist when said wrist brace is being worn by said person;

at least one elongated reinforcement member made of substantially rigid material for supporting said wrist against excessive bending and being housed along said tube outside surface;

a strip of multiple tiny loons affixed on said tube;

at least one strap having a proximal end attached adjacent to one of said first edge and said second edge, a strip of multiple tiny hooks on said strap for securely engaging said multiple tiny loops on said tube to attach said strap to said outer surface of said tube and maintain said web in said closed position;

a looped band for receiving a remote end of said strap therethrough, a strip of multiple tiny loops attached to an interior surface of said looped band for engaging said multiple tiny hooks on said strap to secure said looped band to said strap, and a strip of multiple tiny hooks attached to an exterior surface of said looped band for engaging said strip of multiple tiny loops on said tube to secure the looped band to said tube, said looped band comprising a band with a proximate end and a remote end;

a time piece removably attached to a portion of said looped band, said time piece including a first dowel setting supporting a first dowel and a second dowel setting supporting a second dowel each on opposed sides of said time piece, a first arm extending from said proximate end of said looped band to secure said first dowel and a second arm extending from said proximate end to secure said second dowel to attach said time piece to said proximate end, and a strip of multiple tiny hooks being attached to said proximate end of said band to engage a strip of multiple tiny loops attached to said remote end of said band to form a closed loop.

6. The wrist brace of claim 5 wherein said first arm and said second arm are angled with respect to said band, so the time Piece is assembled at an angle with respect to said band.

* * * * *